United States Patent [19]
Yip

[11] Patent Number: 6,043,043
[45] Date of Patent: Mar. 28, 2000

[54] METHOD FOR THE DETERMINATION OF HEMOGLOBIN ADDUCTS

[75] Inventor: Kin-Fai Yip, Elkhart, Ind.

[73] Assignee: Bayer Corporation, Elkhart, Ind.

[21] Appl. No.: 08/077,546

[22] Filed: Jun. 18, 1993

Related U.S. Application Data

[63] Continuation-in-part of application No. 08/041,471, Apr. 2, 1993, abandoned.

[51] Int. Cl.$^7$ .......................... G01N 33/53; G01N 31/00; G01N 33/72; G01N 15/06
[52] U.S. Cl. .............................. 435/7.2; 435/21; 435/25; 435/26; 436/15; 436/66; 436/67; 436/518; 436/534; 422/68.1; 600/328
[58] Field of Search ..................................... 436/518, 528, 436/534, 66, 67, 807, 15; 422/68.1, 73; 600/328; 435/7.2, 21, 25, 26

[56] References Cited

U.S. PATENT DOCUMENTS

| | | | |
|---|---|---|---|
| 4,658,022 | 4/1987 | Knowles et al. | 530/402 |
| 4,835,097 | 5/1989 | Saunders | 435/4 |
| 4,837,170 | 6/1989 | Ohe et al. | 436/548 |
| 4,970,171 | 11/1990 | Messenger et al. | 436/66 |

OTHER PUBLICATIONS

Little et al Clin. Chem. 32/2, pp. 358–360(1986) "Interlaboratory Standardization of Glycoted Hemoglobin Determinants".

Standing et al Ann. Clin. Biochem. 29 494–505 (1992) "Glycoted Haemoglobin; an Assessment of High Capacity Liquid Chromatographic & Immunoassay Methods,".

Morrero et al Diabetes Care 15 #8 pp. 1045–1049 (Aug. 1992) "Immediate HbAic Results".

Rodgers in *Practical Immunoassay* ed–Butt, Marcel Dekker Inc. (1984)pp. 253–307 "Data Analysis and Quality Control of Assays! A Practical Primer".

*Primary Examiner*—Bennett Celsa
*Assistant Examiner*—Joseph W. Ricigliano
*Attorney, Agent, or Firm*—Jerome L. Jeffers

[57] ABSTRACT

Disclosed is an improvement to the method of determining the concentration of a hemoglobin adduct in a blood sample by the steps of assaying the blood sample for the total amount of hemoglobin, assaying the blood sample for the hemoglobin adduct, and dividing the hemoglobin adduct concentration by the total hemoglobin concentration. The improvement involves normalizing the measurement of the hemoglobin adduct to the total amount of hemoglobin in the blood sample.

19 Claims, 4 Drawing Sheets

METHOD FOR THE DETERMINATION OF HEMOGLOBIN ADDUCTS

This application is a continuation-in-part of application Ser. No. 08/041,471 filed on Apr. 2, 1993 now abandonded.

BACKGROUND OF THE INVENTION

The level of glycation of certain circulating proteins, e.g. hemoglobin, can be used to monitor the average blood glucose because glycation is a non-enzymatic, slow and continuous reaction that is primarily dependent on the ambient glucose concentration to which the hemoglobin is exposed during its residence time in the circulatory system. These two factors, glucose concentration and residence time, translate in vivo to the degree and duration of increased blood glucose concentration (hyperglycemia). Thus, when the blood glucose level is elevated, as it is in diabetic people whose diabetes is not well controlled, increased amounts of glycated hemoglobin are formed. The amount of glycated hemoglobin in an individual's blood reflects the average blood glucose concentration to which hemoglobin has been exposed during its life in the circulatory system. This period is about 100 days, so the determination of the concentration of glycated hemoglobin can provide an historical picture of the individual's blood glucose profile.

Methods described for the measurement of glycated hemoglobin include chromatography on an ion exchange column or boronate affinity columns, HPLC and agarose gel electrophoresis. Each of these techniques has drawbacks with respect to complexity, costly instrumentation, accuracy or variability.

Immuno techniques are available whereby monoclonal antibodies have been developed to react with epitopes of the glycated hemoglobin, i.e. that derivative of hemoglobin formed by the nonenzymatic reaction of glucose with reactive amine groups on the hemoglobin protein, and facilitate the determination of glycated hemoglobin concentration by standard immunochemistry techniques such as ELISA or a latex agglutination assay. Such an agglutination assay is disclosed in U.S. Pat. No. 4,970,171 wherein there is described an immunoassay for glycated hemoglobin, e.g. HbA1c, a variety of hemoglobin with glycation at the β subunit in a blood sample, which involves the steps of:

a) treating the blood sample with a thiocyanate salt capable of denaturing the hemoglobin contained therein and an oxidant capable of converting the hemoglobin in the treated blood sample to the methemoglobin form;

b) assaying the treated sample for met-hemoglobin as representing the amount of total hemoglobin in the sample;

c) assaying the denatured, oxidized blood sample by immunoassay for the amount of denatured form of the particular hemoglobin derivative being sought; and d) calculating the relative amount of hemoglobin that is in the form of the hemoglobin derivative being sought compared to the total amount of hemoglobin in the test sample.

This glycated protein immunoassay was found to have a latent defect which affected its accuracy, which defect is based on the discovery that the response of a given concentration of glycated hemoglobin is not only dependent on its concentration but is also dependent on the total hemoglobin concentration. It has been discovered that there is an inverse relationship between the apparent glycated hemoglobin concentration and the total hemoglobin concentration, i.e. when the total hemoglobin concentration is high, the apparent glycated hemoglobin concentration is less than expected and when total hemoglobin concentration is low the apparent glycated hemoglobin concentration is higher than expected. The same phenomena is observed in the course of determining the concentration of other hemoglobin adducts by equilibrium analytical methods in which the equilibrium of the dimeric form and tetrameric form of the hemoglobin molecule is not perturbed by the chemistry. Immuno, enzymatic and chemical analytical methods are regarded as equilibrium methods whereas chromatographic and pepsin digestion methods are not. The present invention is predicated on the discovery of the underlying reason for this effect and the development of a method to overcome it.

SUMMARY OF THE INVENTION

The present invention is an improved method for determination of hemoglobin adducts, e.g. hemoglobin-acetaldehyde; hemoglobin-urea; hemoglobin-aspirin; hemoglobin-glucose-6-phosphate; hemoglobin-glucose-1,6-diphosphate; hemoglobin-glutathion and hemoglobin-glycation end products, in a blood sample which method comprises the steps of:

a) assaying the blood sample for the total amount of hemoglobin present therein;

b) assaying the blood sample for the amount of hemoglobin adduct present therein;

c) normalizing the measurement from the hemoglobin adduct assay to the amount of total hemoglobin in the sample; and d) dividing the normalized hemoglobin adduct concentration by the total hemoglobin concentration to obtain the corrected concentration of hemoglobin adduct.

DESCRIPTION OF THE INVENTION

Figure 1:
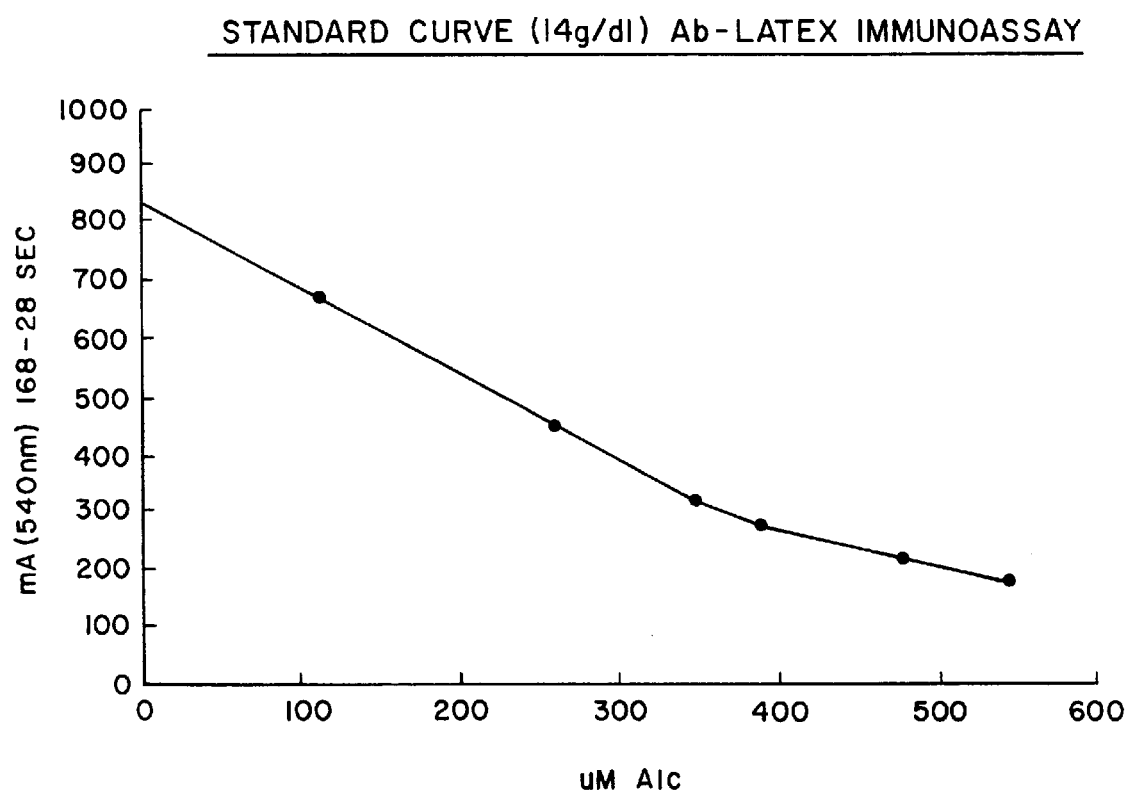
FIG. 1 is a standard curve of an immunoassay for hemoglobin A1c. The curve was generated using six calibrators having different percentages of HbA1c but with the same hemoglobin concentration of 14 g/dL.

Although the normalization procedure can be applied to any assay which, unlike chromatography, does not completely dissociate the hemoglobin molecule, the present invention is particularly useful for the determination of glycated hemoglobin, e.g. HbA1c, by immunoassay techniques. Other pre-equilibrium assay methods which may be used include enzymatic, e.g. those involving the use of oxidases, reductases or phosphatases that can interact with the glucose, glucose-6-phosphate or glucose-1,6-diphosphate in the adduct; and chemical, e.g. those involving chemical reactions that can oxidize, reduce or hydrolyze the adduct. More specifically, the glucose portion of the hemoglobin-glucose adduct can be liberated as 5-hydroxymethylfurfural by acid treatment. The 5-hydroxymethylfurfural is then reacted with thiobarbituric acid to form a colored complex. The color intensity of the complex is proportional to the concentration of the hemoglobin-glucose adduct present in the sample. Another example of chemical determination is the analysis of the adduct formed by acetaldehyde and hemoglobin. Acetaldehyde, the first metabolite of ethanol, has been shown to form adducts with hemoglobin and the measurement of hemoglobin associated acetaldehyde has been reported to distinguish between drinking and non-drinking individuals. The acetaldehyde in the adduct can be hydrolyzed and then reacted with 1,3-cyclohexandeione to form a fluorophore which is analyzed quantitatively. The fluorophore's concentration is proportional to the concentration of the hemoglobin-acetaldehyde adduct present in the sample. These methods for the determination of the hemoglobin adduct typically do not require denaturation of the hemoglobin.

The present invention is based upon the fact that native hemoglobin exists as an equilibrium of tetrameric $\alpha$ and $\beta$ chains ($\alpha 2 \beta 2$) and the dimeric form ($\alpha \beta$). These $\alpha$ and $\beta$ chains are each about 143 amino acids in length. At the end of the $\beta$ subunit there is a valine unit which is part of the hemoglobin A1c epitope and can react with glucose. In a mixture of native hemoglobin and hemoglobin adducts (as in blood) there exists, in the case of glycated hemoglobin, a mixture of un-glycated tetramers, un-glycated dimers, monoglycated tetramers and mono-glycated dimers. All of the glycated components will have different immuno, enzymatic or chemical reactivity; the glycated dimers have the highest reactivity since their glycation sites are exposed and accessible to interaction with the reactant. The glycated tetramers have much lower reactivity because in the tetrameric configuration the glycated site is sterically hindered. When the total concentration of hemoglobin in the sample increases, the equilibrium between the tetrameric form of glycated hemoglobin and its dimeric form is shifted towards the tetrameric form because at higher concentrations, the associated, tetrameric form is thermodynamically favored. The combination of this equilibrium shift and the differences in reactivity between the tetrameric and dimeric forms of glycated hemoglobin with the antibody reagent cause the assay to be affected by the total amount of hemoglobin present in the blood sample. In the clinical setting, this "hemoglobin dependency effect", which is a bias based on the total amount of hemoglobin present in the sample, should be taken into account when the concentration of the hemoglobin adduct is being determined.

Depending on the hemoglobin adduct whose presence or concentration is being sought and the particular method used in its assay, it may be necessary to expose the reactive site of the hemoglobin adduct by denaturation. The term denaturation, as used herein, is intended to mean any treatment which will expose the reactive site to the analytical reagent selected for use without disrupting the equilibrium between the dimeric and tetrameric hemoglobin chains. Suitable denaturation techniques include treating the sample with a high salt concentration; low or high pH; a choatropic reagent such as thiocyanate, guanidinium, urea or a surfactant such as a non-ionic, cationic or anionic detergent. All of these treatments cause the disruption to some degree of the hydrogen bonding of the hemoglobin molecule thereby exposing the reactive site. These treatments do not cause the complete dissociation of the hemoglobin and, therefore, do not alter the aforementioned equilibrium. Proteolytic digestion or chromatography would not be suitable for use in conjunction with the present method since it will disrupt this equilibrium. The determination of glycated hemoglobin, e.g. HbA1c, will typically involve denaturation of the hemoglobin, especially when an immunoassay technique is to be employed.

The method of the present invention, in which an immunoassay and a glycated hemoglobin are chosen for purposes of illustration, is carried out as follows:

In the first step, the hemoglobin is denatured in order that the glycated N-terminal peptide residue becomes available for antibody binding. In U.S. Pat. No. 4,658,022 there are described numerous techniques for protein denaturation including treatment of the protein by physical means such as heat, sonication, high and low pH and chemical denaturation by digestion or interaction with a chaotropic agent such as guanidine, urea or a detergent such as sodium dodecylsulfate. In a preferred technique, the protein is denatured to expose the peptide epitope for antibody bonding by treating the blood sample with a thiocyanate salt and an oxidant as disclosed in U.S. Pat. No. 4,970,171 incorporated herein by reference. The technique taught in this patent oxidizes the hemoglobin to met-hemoglobin which is converted to thiocyan-met-hemoglobin as the stable color component, i.e. the color intensity is correlated to the concentration of the hemoglobin. The resulting thiocyan-met-hemoglobin serves as the basis for measuring total sample hemoglobin with the denatured form of the particular hemoglobin derivative serving as the analyte in the immunoassay part of the procedure. The thiocyanate salt is selected from those salts which upon ionization provide the thiocyanate anion ($SCN^-$) to render the hemoglobin suitable for detection in the immunoassay. Ammonium, sodium and potassium are suitable countercations. Lithium thiocyanate provides faster denaturation as well as expedited lysing of red blood cells in the blood sample being tested. The oxidant, which can be essentially any inorganic oxidizing agent, converts the native hemoglobin ferrous ion to its ferric met-hemoglobin form. Suitable oxidants include ferricyanide, iodate, chlorate, bromate, chromate, hypochlorite, iodate, periodate and peroxide.

Met-hemoglobin concentration is conveniently determined by measuring its characteristic absorbance at 540 nanometers using a conventional spectrophotometer such as the HP 8450A spectrophotometer or its equivalent. Alternatively, one can use the Drabkin's procedure as described in National Commission for Clinical Laboratory Standards of the United States, Proposed Standard PSH-15.

After denaturation, the blood sample is assayed for total met-hemoglobin and for the hemoglobin adduct of interest. This is most conveniently accomplished by immunoassay using monoclonal antibodies developed to bind specifically to the epitope that characterizes the hemoglobin adduct, e.g. hemoglobin A1c, in the denatured protein. The particular immunoassay technique and format, as well as the labeling approach and detection signal generated, is not critical. Radioisotopic or enzyme labeled (ELISA) techniques can be used. A particle agglutination inhibition immunoassay based on the specific interaction of an antibody particle reagent and an agglutinator reagent is particularly useful. The antibody particle reagent comprises the monoclonal antibody, or a fragment thereof, bound to a water suspensible particle, typically a polystyrene or other latex. The agglutinator comprises a plurality of epitopic binding sites for the antibody reagent. In the absence of analyte, the antibody particle and agglutinator bind to one another to form a light scattering complex that can be quantified by turbidimetric measurement. In the presence of increasing amounts of analyte, the turbidity of the solution decreases as antibody particles become bound to the analyte and cannot bind to the agglutinator which is typically a polymer backbone to which is attached a number of organic moieties, such as peptide residues, which define the epitope that characterizes the hemoglobin derivative of interest. When hemoglobin A1c is to be determined, the epitope comprises the glycated peptide residues of a few amino acid units corresponding to the sequence of the glycated N-terminal residue in hemoglobin A1c.

After the concentration of total hemoglobin and the hemoglobin derivative are determined, the percentage of the hemoglobin adduct as a portion of total hemoglobin is calculated. This determination, as taught in the prior art, is carried out by simply dividing the hemoglobin derivative concentration by the concentratior of total hemoglobin to arrive at the percentage value of the hemoglobin adduct. This calculation does not provide a totally accurate picture, however, due to the previously mentioned hemoglobin dependency effect. It is an object of the present invention to provide a procedure for factoring the hemoglobin dependency effect out of the determination of the hemoglobin derivative to thereby provide a more accurate procedure for determining the concentration of the hemoglobin derivative under consideration. This improved procedure involves normalizing the concentration of the hemoglobin derivative as determined by the assay. This is accomplished by deducing the true concentration of hemoglobin derivative from its reactivity and the total concentration of hemoglobin, both of which values are determined during the assay. The normalization procedure is carried out in 5 steps. These steps are:

A. Creating a calibration curve relating (a) the concentration of the hemoglobin adduct as determined by a reference procedure, such as HPLC, which is not subject to the hemoglobin effect to (b) the immuno reaction response by using calibrator blood samples containing a normalized concentration of hemoglobin and different concentrations of the hemoglobin adduct;

B. Preparing a series of blood samples containing different concentrations of hemoglobin but the same percentage of hemoglobin adduct in each series, determining the immunoreaction response from each sample and obtaining the observed concentration of hemoglobin adduct for each sample from the calibration curve generated in Step A;

C. Creating a series of polynomial ($n^{th}$ order) fitted curves relating (a) the observed concentration of hemoglobin adduct from each series as determined in Step B to (b) the concentration of hemoglobin in each sample in the series, obtaining the polynomial curve fitting coefficients ($a_n, a_{n-1}, a_{n-2} \ldots a_o$) for each curve and repeating the process for the whole series of curves;

D. Obtaining the linear curve fitting relating (a) the polynomial curve fitting coefficient $a_n$ for the series of curves generated in Step C to (b) the percentage of hemoglobin adduct at the normalized concentration of hemoglobin and obtaining the slope ($S_n$) and intercept ($I_n$) of the linear curve fit;

E. Obtaining the $S_{n-1}, S_{n-2} \ldots S_1$ and $I_{n-1}, I_{n-2} \ldots I_1$ values from the polynomial curve fitting coefficient $a_{n-1}, a_{n-2} \ldots a_1$ respectively by the procedure of step D; and F. Obtaining the corrected hemoglobin adduct concentration by relating (a) the observed hemoglobin adduct concentration to (b) hemoglobin concentration by solving the equation:

$$Hb_{ad} = (Hb_{ad}' - (Hb^n - 14^n) * I_n - (Hb^{n-1} - 14^{n-1})$$

$$* I_{n-1} - (Hb^{n-2} - 14^{n-2}) * I_{n-2} - \ldots (Hb-14)$$

$$* I_1) / ((Hb^n - 14^n) - *S_n + (Hb^{n-1} - 14^{n-1}) * S_{n-1} +$$

$$(Hb^{n-2} - 14^{n-2}) * S_{n-2} + \ldots - (Hb - 14) * S_1 + 1).$$

where:
$Hb_{ad}$ is the corrected concentration of the hemoglobin adduct whose concentration is being sought;
$Hb_{ad}'$ is the observed concentration of hemoglobin adduct as determined by immunoassay;
Hb is the total hemoglobin concentration in terms of g/dL;
$I_n \ldots I_1$ and $S_n \ldots S_1$ are experimentally determined coefficients; and where 14 represents 14 g/dL hemoglobin selected as the normalized concentration. Normalized concentration, as used herein means a fixed concentration of hemoglobin. Any concentration can be selected as the normalized concentration, however, 14 g/dL is preferred for use in this procedure because the majority of clinical blood specimens will contain this concentration of hemoglobin. The advantage in this is that, if the specimen's hemoglobin concentration is equal to the normalized concentration, no correction is required, since, in that case, the corrected concentration is equal to the observed concentration.

The method of practicing the present invention is further illustrated by the following example in which HbA1c is the hemoglobin adduct of interest. In this example the second order polynomial is selected for illustration purposes. One can use a linear, $2^{nd}$ order or higher order polynomial curve fit in this procedure. However, the linear curve fit will not correct the curvature of the results and the algorithm for higher order polynomials will be more complicated and carry more coefficients, i.e. the linear fit will require coefficients $I_1$ and $S_1$; the second order polynomial will require coefficients $I_1, I_2, S_1$ and $S_2$ while the third order polynomial will require coefficients $I_1, I_2, I_3, S_1, S_2$ and $S_3$.

EXAMPLE

A. Six calibrators were prepared containing 2.5%, 5.9%, 7.9%, 8.93%, 10.97% and 12.54% hemoglobin A1c respectively as determined by HPLC. The total hemoglobin concentration in each calibrator blood sample was 14 g/dL. The immunoreaction response of each calibrator was measured by the latex agglutination technique previously described with the results being set out in Table I.

TABLE I

| % A1c | 14 g/dL A1c (mM) | mA |
|---|---|---|
| 0 | 0 | 827.9 |
| 2.5% | 108.5 | 670.5 |
| 5.93% | 257.4 | 440.2 |
| 7.97% | 345.9 | 321.7 |
| 8.93% | 387.6 | 271.6 |
| 10.97% | 476.1 | 212.3 |
| 12.54% | 544.2 | 173.4 |

The immunoreaction responses were used to generate the calibration curve of FIG. 1 with the immunoreaction responses being used as the Y values and the reference A1c concentrations used as the X values. In this example, the immunoreaction response is represented by mA (540 nm, 168-28) which is the difference in milli-absorbance reading at a wavelength of 540 nanometers between 28 and 168 seconds after start of the reaction, B. The next step was to prepare six groups of samples containing 2.5%, 5.93%, 7.97%, 8.93%, 10.97% and 12.54% A1c (corresponding to the HbA1c levels found by the reference method in step A) each of which group having 5 or more levels of hemoglobin concentration between 9 and 20 g/dL. These samples were prepared from packed human red blood cells and human plasma. Their immunoreaction responses were measured by the latex agglutination method previously described and from the immunoreaction responses, the A1c concentrations of these samples were calculated using the calibration curve generated in Step A. The sample concentrations are shown in Table II as observed A1c values. The procedure for measuring HbA1c is described in detail in U.S. Pat. No. 4,847,209 as well as how $\mu$M HbA1c relates to % HbA1c. The teachings of this patent are incorporated herein by reference.

Figure 2:
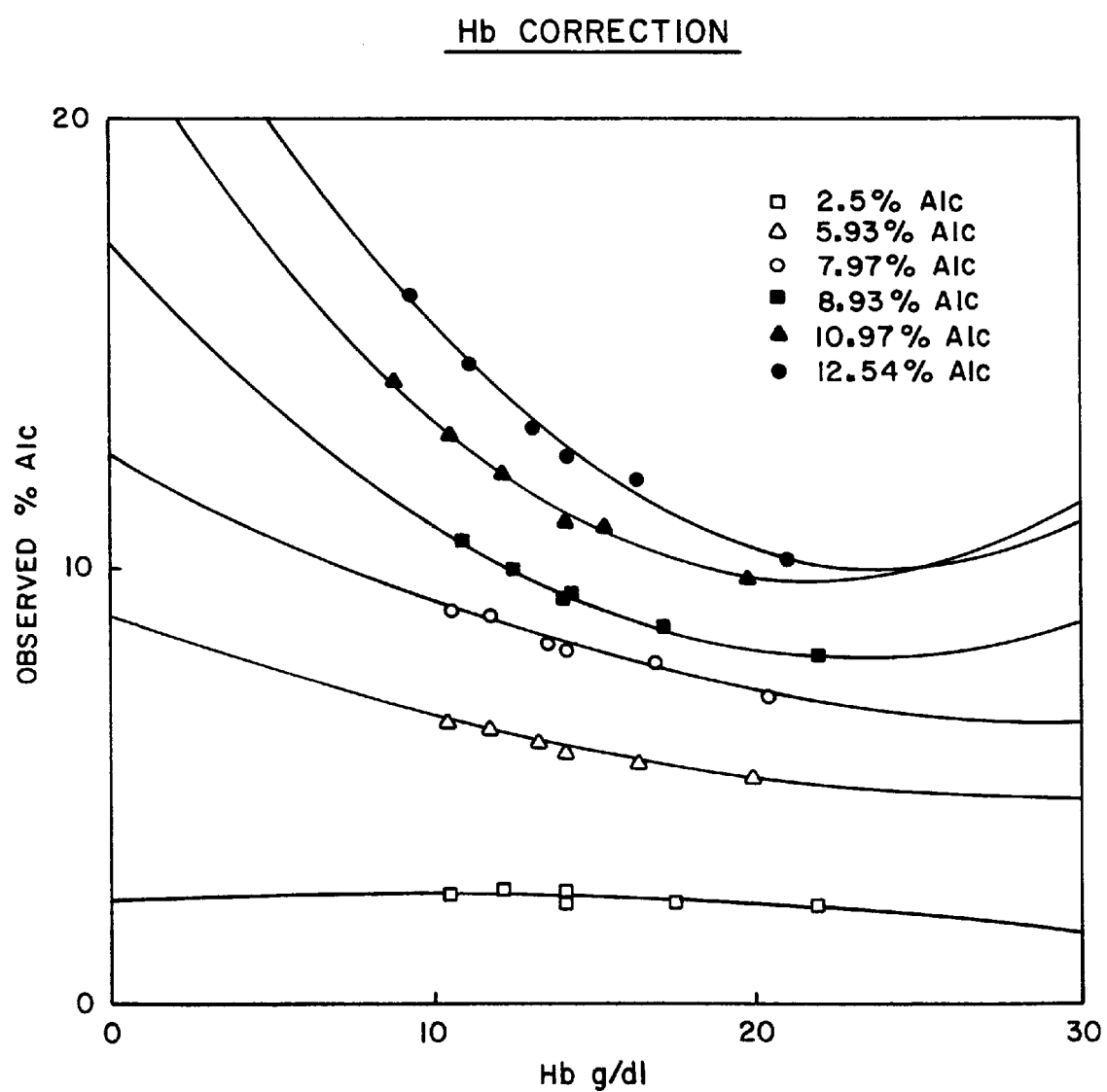
FIG. 2 illustrates the dependence of the observed percentage of HbA1c in terms of total hemoglobin concentration as determined by the immunoassay. It also shows the second order polynomial data fitting of the observed percentage of HbA1c at different HbA1c levels.

C. For each group of samples in Step B, the observed % A1c values were plotted against the hemoglobin concentration (FIG. 2). Using the observed % A1c values as Y values and the hemoglobin concentration as X values (Table II), the data can be fitted with the polynomial curve fit using a commercial curve fitting program such as SlideWrite© from Advance Graphic Software Inc. or Sigmaplot© from Jandel Scientific. The data can be fitted with any order polynomial.

For the group of 2.5% samples, the observed % A1c values of 2.28, 2.43, 2.57, 2.43, 2.75 and 2.5 were used as the Y values and the hemoglobin concentration of 21.9, 17.5, 14, 14, 12.1, 10.4 were used as the X values. After the $2^{nd}$ order polynomial curve fitting of these data, the equation $Y=-0.0011617*X^2+0.02542*-X+2.490$ was generated for the group of samples.

For the group of 5.93% samples, the observed % A1c values of 5.17, 5.58, 5.79, 6.06, 6.35 and 6.45 were used as the Y values and the hemoglobin concentration of 19.9, 16.3, 14, 13.2, 11.7 and 10.3 were used as the X values. After the $2^{nd}$ order polynomial curve fitting of these data, the equation $Y=0.004478*X^2-0.2747*-X+8.859$ was generated for this group of samples.

For the group of 7.97% samples, the observed % A1c values of 7.05, 7.88, 8.05, 8.26, 8.87 and 9.08 were used as the Y values and the hemoglobin concentration of 20.4, 16.8, 14, 13.4 11.6 and 10.4 were used as the X values. After the $2^{nd}$ order polynomial curve fitting of these data, the equation $Y=0.006158*X^2-0.3860*-X+12.419$ was generated for this group of samples.

For the group of 8.93% samples, the observed A1c values of 7.92, 8.60, 9.33, 9.26, 9.92 and 10.58 were used as the Y values and the hemoglobin concentration of 21.9, 17.1, 14.2, 14, 12.3 and 10.8 were used as the X values. After the $2^{nd}$ order polynomial curve fitting of these data, the equation $Y=0.017231*X^2-0.7985*-X+17.158$ was generated for this group of samples.

For the group of 10.97% samples, the observed % A1c values of 9.72, 10.94, 11.02, 12.14, 12.96 and 14.13 were used as the Y values and the hemoglobin concentration of 19.7, 15.2, 14, 12, 10.4, 8.7 were used as the X values. After the $2^{nd}$ order polynomial curve fitting of these data, the equation $Y=0.01644*-X^2-1.14462*X+11.064$ was generated for this group of samples.

For the group of 12.54% samples, the observed % A1c values of 10.13, 11.97, 12.44, 13.08, 14.46 and 16.01 were used as the Y values and the hemoglobin concentration of 20.9, 16.2, 14, 13, 11 and 9.2 were used as the X values. After the $2^{nd}$ order polynomial curve fitting of these data, the equation $Y=0.02734*-X^2-1.3086*X+25.608$ was generated for this group of samples.

In these second order equations; -0.001617, 0.004478, 0.006158, 0.017231, 0.02644 and 0.02734 are the $a_2$ coefficients and 0.02542, -0.2747, -0.386, -0.7985, -1.1462 and -1.3086 are the $a_1$ coefficients generated from the curve fitting steps. The procedures of steps D and E require the use of these $a_1$ and $a_2$ coefficients for further calculation.

Figure 3:
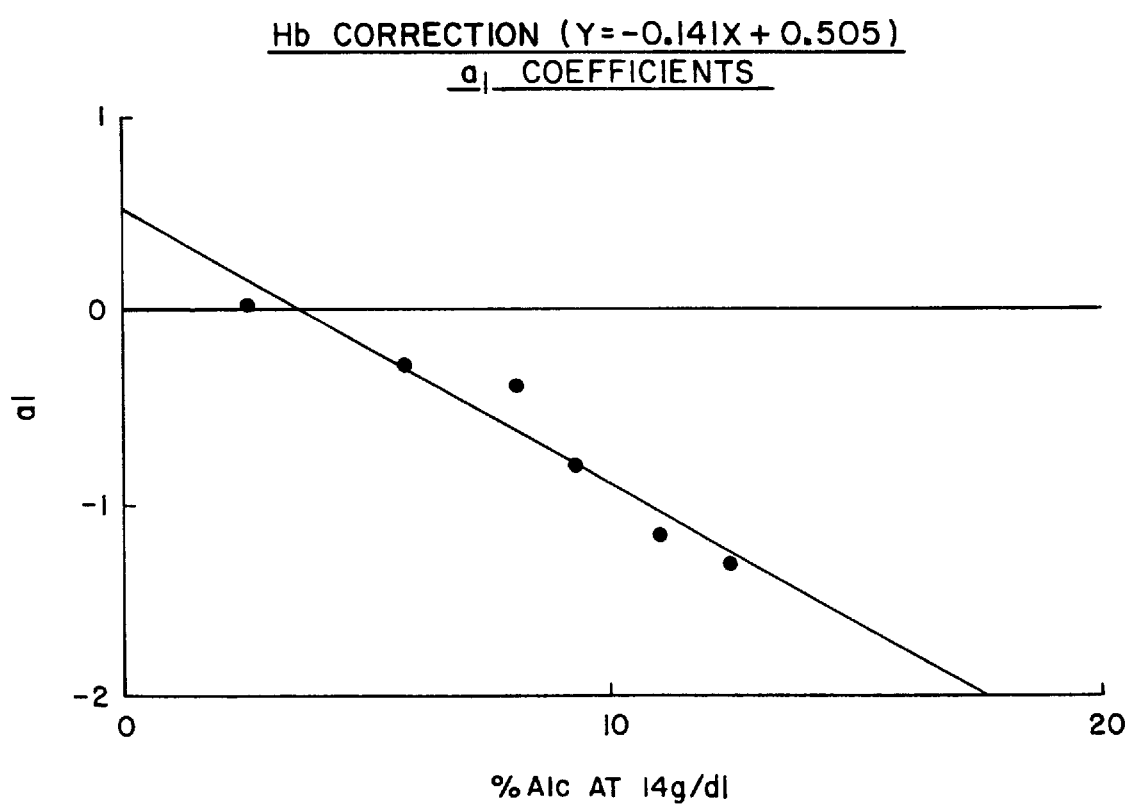
FIG. 3 shows the a, coefficients at different levels of HbA1c. It also illustrates the linear data fit of the $a_2$ coefficients. The intercept of the linear fit is the $I_2$ coefficient and the slope of the linear fit is the $S_2$ coefficient.

D. The $a_1$ values, 0.02542, -0.2747, -0.3860, -0.7985, -1.1462 and -1.3086 were used as the Y values and plotted against the % A1c values of 2.5, 5.93, 7.97, 8.93, 10.97 and 12.54 as the X values to prepare FIG. 3. The data were fit with a linear curve fit using the Slidewrite© curve fitting program. This linear curve fitting gives the result of:

$$Y=-0.141*X+0.505$$

where, -0.141 is the $S_1$ coefficient and 0.505 is the $I_1$ coefficient.

Figure 4:
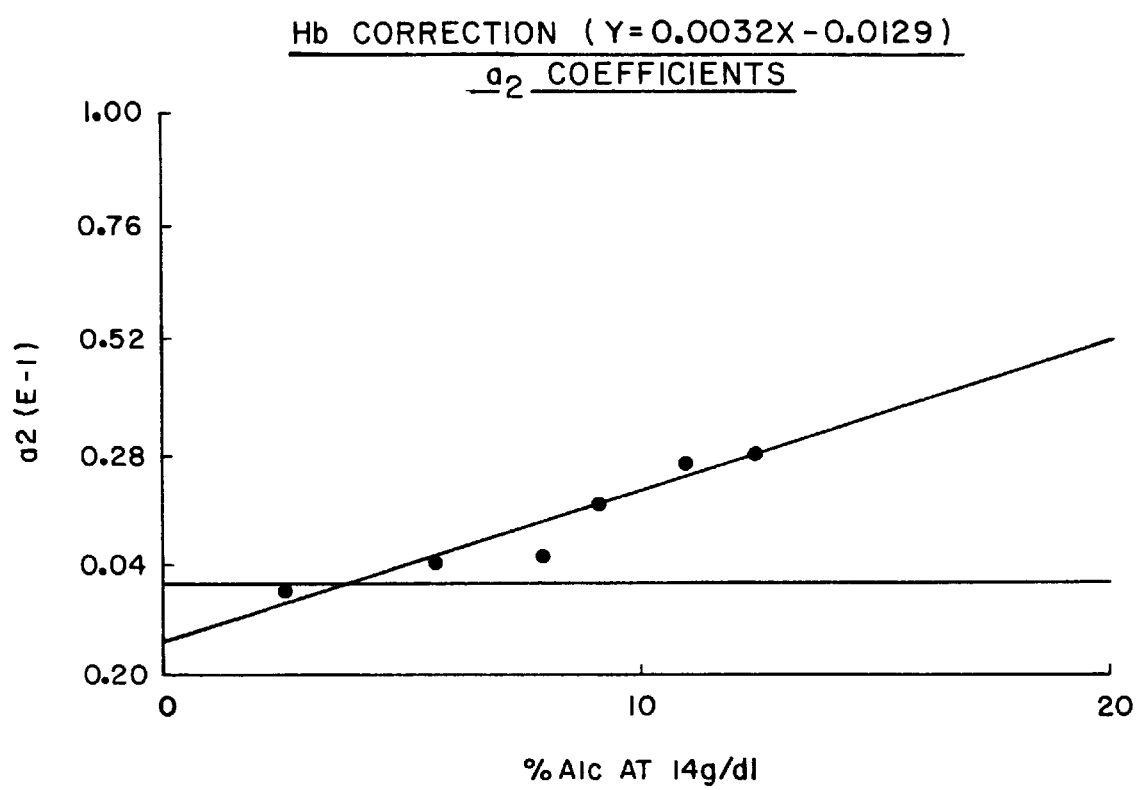
FIG. 4 shows the $a_2$ coefficients at different levels of HbA1c. It also shows the linear data fit of the $a_2$ coefficients. The intercept of the linear fit is the $I_2$ coefficient and the slope of the linear fit is the $S_2$ coefficient.

E. The $a_2$ values -0.001617, 0.004478, 0.006158, 0.017231, 0.02644 and 0.02734 were used as the Y values and plotted against the % A1c values of 2.5, 5.93, 7.97, 8.93, 10.97 and 12.54 as the X values to prepare FIG. 4. The data were fit with a linear curve fit to give the result of:

$$Y=0.0032*X -0.0129$$

where 0.0032 is the $S_2$ coefficient and 00.0129 is the $I_2$ coefficient.

F. The corrected A1c concentration was obtained by solving the equation:

$$A1c=(A1c'-(Hb^2-14^2)*I_2-(Hb-14)*I_1)/((Hb^2-14^2)-*S_2+(Hb-14)*S_1+1) \qquad \text{(Equation I)}$$

where:
A1c' is the observed % HbA1c as determined by the immunoassay;

Hb is the total hemoglobin concentration in terms of g/dL;

$I_2$, $I_1$, $S_2$ and $S_1$ are experimentally determined coefficients, and 14 is 14 g/dL hemoglobin selected as the normalized concentration.

When the concentration of hemoglobin is further away from the normalized concentration, more bias of the HbA1c value from the reference value (e.g. HPLC value) is observed. Therefore, it is advantageous to set the normalized concentration to the concentration of hemoglobin that is most commonly encountered in the blood sample being examined to provide a test having the least bias. This correction method can be used with various normalized concentrations, e.g. 13 g/dL, 14 g/dL, 15 g/dL, etc. However, since the majority of blood specimens will have a hemoglobin concentration of 14 g/dL, it is advantageous to select this level as the normalized concentration.

In the foregoing example there is described the determination of the hemoglobin A1c epitope, however, the technique of the present invention is equally applicable to the determination of other hemoglobin derivatives, such as those having other glycated amine epitopes along the $\alpha$ and $\beta$ subunits. Likewise, the present method is applicable to assay methods other than immunoassay which do not completely dissociate the hemoglobin. These methods include chemical and enzymatic assays.

Referring to Table II which reports the results of this experiment, the bias (% difference between the observed value and the reference value) of the uncorrected results ranged from 28.7% to −18.6%. After correction with the algorithm (Equation I) and the above coefficients, the bias were reduced to 7.0 to −5.6%.

The instrument contains a memory which is preprogrammed to do all of the calculations necessary for normalizing the measured concentration of the hemoglobin adduct to the total amount of hemoglobin in the blood sample.

TABLE II

Hemoglobin Correction for HbA1c Determined by Latex Bound Antibody Agglutination Method

| Reference A1c Values | Observed Hb Concentrations | Observed % A1c Values | % Bias from Reference Values | % A1c After Correction | % Bias from Reference Values After Correction |
|---|---|---|---|---|---|
| 2.5% | 21.9 | 2.28 | −11.3 | 2.46 | −4.4 |
| | 17.5 | 2.43 | −5.4 | 2.43 | −5.6 |
| | 14 | 2.57 | 0.0 | 2.57 | 0.0 |
| | 14 | 2.43 | −5.4 | 2.43 | −5.4 |
| | 12.1 | 2.73 | 6.2 | 2.75 | 7.0 |
| | 10.4 | 2.5 | −2.7 | 2.60 | 1.0 |
| 5.93% | 19.9 | 5.17 | −10.7 | 5.90 | 2.0 |
| | 16.3 | 5.58 | −3.6 | 5.92 | 2.2 |
| | 14 | 5.79 | 0.0 | 5.79 | 0.0 |
| | 13.2 | 6.06 | 4.7 | 5.93 | 2.4 |
| | 11.7 | 6.35 | 9.7 | 5.95 | 2.7 |
| | 10.3 | 6.45 | 11.4 | 5.80 | 0.2 |
| 7.97% | 20.4 | 7.05 | −12.4 | 8.30 | 3.1 |
| | 16.8 | 7.88 | −2.1 | 8.60 | 6.8 |
| | 14 | 8.05 | 0.0 | 8.05 | 0.0 |
| | 13.4 | 8.26 | 2.6 | 8.09 | 0.5 |
| | 11.6 | 8.87 | 10.2 | 8.14 | 1.1 |
| | 10.4 | 9.08 | 12.8 | 7.96 | −1.1 |
| 8.93% | 21.9 | 7.92 | −14.5 | 9.56 | 3.3 |
| | 17.1 | 8.6 | −7.1 | 9.50 | 2.6 |
| | 14.2 | 9.33 | 0.8 | 9.40 | 1.5 |
| | 14 | 9.26 | 0.0 | 9.26 | 0.0 |
| | 12.3 | 9.92 | 7.1 | 9.30 | 0.5 |
| | 10.8 | 10.58 | 14.3 | 9.33 | 0.8 |
| 10.97% | 19.7 | 9.72 | −11.8 | 11.49 | 4.3 |
| | 15.2 | 10.94 | −0.7 | 11.44 | 3.8 |
| | 14 | 11.02 | 0.0 | 11.02 | 0.0 |
| | 12 | 12.14 | 10.2 | 11.19 | 1.5 |
| | 10.4 | 12.96 | 17.6 | 11.12 | 1.0 |
| | 8.7 | 14.13 | 28.2 | 11.20 | 1.6 |
| 12.54% | 20.9 | 10.13 | −18.6 | 12.23 | −1.7 |
| | 16.2 | 11.97 | −3.8 | 12.98 | 4.4 |
| | 14 | 12.44 | 0.0 | 12.44 | 0.0 |
| | 13 | 13.08 | 5.1 | 12.55 | 0.9 |
| | 11 | 14.46 | 16.2 | 12.69 | 2.0 |
| | 9.2 | 16.01 | 28.7 | 12.87 | 3.5 |

% Bias Calculated Against 14 g/dL Values

The normalization for hemoglobin concentration step of the present invention can be carried out by means of a pre-programmed computer memory which may be n the form of a microchip. Incorporating the microchip into a known device for the determination of a preselected hemoglobin adduct, such as that described in Diabetes Care, D.G. Marrero, et al 15/8 1045–1049 (1992), provides a device comprising a) means for determining the total amount of hemoglobin in the blood sample;

b) means for carrying out an assay of the hemoglobin adduct;

c) means for normalizing the measurement of the hemoglobin adduct to the total amount of hemoglobin in the sample; and d) means for dividing the normalized hemoglobin adduct concentration by the total hemoglobin concentration to obtain the corrected concentration of the hemoglobin adduct.

When the hemoglobin adduct involved and/or the assay method are such that denaturation of the hemoglobin are required, the device will also include means for denaturing the hemoglobin.

The mathematical equation, e.g. Equation I and the I and S coefficients can be programmed into and stored in the memory of a calculation device such as a calculator, computer or computer that has been interfaced with a clinical analyzer capable of determining the total concentration of hemoglobin and that of the hemoglobin adduct. For each clinical sample, the observed concentration of hemoglobin adduct and total hemoglobin concentration is determined by running the assay. The corrected hemoglobin adduct concentration is then determined either manually using the calculator or by means of the pre-programmed computer. Alternatively the results can be obtained directly from a computer that has been interfaced with the clinical analyzer.

What is claimed is:

1. A method for the determination of a particular hemoglobin adduct in a blood sample which method comprises the steps of:

a) assaying the blood sample for the total amount of hemoglobin present therein;

b) assaying the blood sample by an assay technique which is subject to bias based on the total amount of hemoglobin in the blood sample and which is specific for the hemoglobin adduct whose concentration is being determined;

c) normalizing the measurement of the hemoglobin adduct to the total amount of hemoglobin in the sample by:
  i. Creating a calibration curve relation (a) the concentration of the hemoglobin adduct as determined by a reference procedure which is not subject to bias based on the total amount of hemoglobin in the blood sample to (b) the response obtained by analiyzing calibrator blood samples for the hemoglobin adduct using a method which is subject to bias based on the total amount of hemoglobin in the blood sample;
  ii. Providing a series of blood samples containing different concentrations of hemoglobin with the same concentration of hemoglobin adduct in each sample, determining the concentration of the adduct by the method which is subject to bias and obtaining the observed concentration of hemoglobin adduct for each sample from the calibration curve generated in step A;
  iii. Creating a series of polynomial ($n^{th}$ order) fitted curves relation (a) the observed concentration of hemoglobin adduct from each series as determined in step B to (b) the concentration of hemoglobin in each sample in the series, obtaining the polynomial curve fitting coefficients ($a_n$, $a_{n-1}$, $a_{n-2}$ ... $a_0$) for each curve and repeating the process for the whole series of curves;
  iv. Obtaining the linear curve fitting relation (a) the polynomial curve fitting coefficient $a_n$ for the series of curves generated in step C to (b) the percentage of hemoglobin at a normalized concentration of hemoglobin and obtaining the slope ($S_n$) and intercept ($I_n$) of the linear curve fit;
  v. Obtaining the $S_{n-1}$, $S_{n-2}$ ... $S_1$ and $I_{n-1}$, $I_{n-2}$ ... $I_1$ values from the polynomial curve fitting coefficient $a_{n-1}$, $a_{n-2}$ ... $a_1$ respectively; and
  vi. Obtaining the corrected hemoglobin adduct conedntration by relating (a) the observed hemoglobin adduct concentration to (b) the observed total hemoglobin concentration by solving the equation:

$$Hb_{ad} = (Hb_{ad'} - (HB^n - N^n) * I_n - (Hb^{n-1} - N^{n-1})$$
$$* I_{n-1} - (Hb^{n-2} - N^{n-2}) * I_{n-2} - \ldots (Hb - N)$$
$$* I^1) / ((Hb^n - N^n) * S_n + -(Hb^{n-1} - N^{n-1})$$
$$IS_{n-1} + (Hb^{n-2} - N^{n-2}) * S_{n-2} + \ldots - (Hb - N) * S_1 + 1)$$

where:
  $Hb_{ad}$ is the corrected concentration of the hemoglobin adduct, the concentration of which is being sought;
  $Hb_{ad'}$ is the observed concentration in terms of g/dL;
  $I_n \ldots I^1$ and $S_n \ldots S_1$ are experimentally determined coefficients; and
  N represents the normalized concentration of hemoglobin in g/dL; and
d) dividing the normalized hemoglobin adduct concentration by the total hemoglobin concentration to obtain the corrected concentration of the hemoglobin adduct.

2. The method of claim 1 wherein the normalized concentration of hemoglobin is 14.

3. The method of claim 1 wherein the hemoglobin adduct is hemoglobin-acetaldehyde; hemoglobin-urea; hemoglobin-aspirin; hemoglobin-glucose-6-phosphate; hemoglobin-glucose-1,6-diphosphate or hemoglobin-glutathion.

4. The method of claim 1 wherein the hemoglobin adduct is glycated hemoglobin.

5. The method of claim 4 wherein the glycated hemoglobin is HbA1c.

6. The method of claim 1 wherein the observed adduct concentration is determined by immunoassay, chemical or enzymatic techniques.

7. The method of claim 6 wherein there is used an enzymatic technique in which the enzyme is a oxidase, reductase or phosphatase.

8. The method of claim 6 wherein there is used a chemical assay involving treating the hemoglobin adduct with 5-hydroxymethylfurfuryl and thiobarbituric acid to form a colored complex.

9. The method of claim 6 wherein the observed adduct concentration is determined by a latex/agglutination immunoassay.

10. The method of any of claims 1 and 2–9 wherein the hemoglobin is denatured before the assay.

11. The method of claim 10 wherein the denaturation. is accomplished by treating the blood sample with a high salt concentration, low or high pH, a choatropic reagent or a surfactant.

12. The method of claim 11 wherein the denaturation reagent is a surfactant.

13. The method of claim 12 wherein the surfactant is a non-ionic, cationic or anionic detergent.

14. The method of claim 1 wherein the polynomial titled curves are of the second order.

15. A method for the determination of $HbA_{1c}$ in a blood sample which comprises the steps of:
a) treating the blood sample with a denaturant capable of denaturing substantially all of the hemoglobin in the sample;
b) assaying the denatured blood sample for the total amount of hemoglobin present therein;
c) assaying the denatured blood sample by an immunoassay technique which is specific for $HbA_{1c}$;
d) normalizing the $HbA_{1c}$ measurement from the immunoassay to the amount of total hemoglobin in the sample by:
  i. Creating a calibration curve relating (a) the concentration of $HbA_{1c}$ as determined by a reference procedure which is not subject to bias based on the total amount of hemoglobin in the blood sample to (b) the response obtained by analyzing calibrator blood samples for $HbA_{1c}$ by immunoassay;
  ii. Providing a series of blood sample containing different concentration of hemoglobin with the same concentration of $HbA_{1c}$ in each sample, determining the concentration of $HbA_{1c}$ by immunoassay and obtaining the observed concentration of $HbA_{1c}$ for each sample from the calibration curve generated in Step A;
  iii. Creating a series of $2^{nd}$ order polynomial fitted curves relation (a) the observed concentration of $HbA_{1c}$ from each series as determined in step B to (b) the concentration of hemoglobin in each sample in the series, obtaining the polynomial curve fitting coefficients for each curve and repeation the process for the whole series of curves;
  iv. Obtaining the linear curve fitting relation (a) the polynomial curve fitting coefficient $a_1$ for the series of curves generated in Step C to (b) the percentage of hemoglobin at a normaized hemoglobin concemtration of 14 g/dL and obtaining the slope ($S_1$) and intercept ($I_1$) of the linear curve fit;
  v. Obtaining the $S_2$ and $I_2$ values from the polynomial curve fitting coefficient $a_1$; and vi. Obtaining the corrected $HbA_{1c}$ concentration by relating (a) the observed $HbA_{1c}$ concentration to (b) the observed total hemoglobin concentration by solving the equation $$A_{1c}=(A_{1c'}-(Hb^2-14^2)*I_2-(Hb-14)*I_1)/((Hb^2-14^2)-*S_2+(Hb-14)*S_1+1)$$

where:

$A_{1c}$ is the corredted $HbA_{1c}$ concentration;

$A_{1c'}$ is the observed $HbA_{1c}$ concentration as determined by the immunoassay;

Hb is the total hemoglobin concentration in terms of g/dL;

$I_2$, $I_1$, $S_2$ and $S_1$ are experimentally determined coefficients, and 14 is 14 g/dL hemoglobin selected as the normalized hemoglobin concentration; and e) dividing the normalized $HbA_{1c}$ concentration by the total hemoglobin concentration to obtain the corrected $HbA_{1c}$ concentration.

16. A device for determining the concentration of a hemoglobin adduct in a blood sample which comprises:

a) means for determining the total amount of hemoglobin in the blood sample;

b) means for determining the concentration of the hemoglobin adduct;

c) a calculating device containing a memory in which the equation $$Hb_{ad}=(Hb_{ad'}-(HB^n-N^n)*I_n-(Hb^{n-1}-N^{n-1})$$

$$*I_{n-1}(Hb^{n-2}-N^{n-2})*I_{n-2}-\ldots$$

$$(Hb0N)*I_1)/((Hb^n-N^n)*D_n+-(Hb^{n-1}-N^{n-1})$$

$$*S_{n-1}+(Hb-2-N^{n-2})*S_{n-1}+\ldots-(Hb-N)*S_1+1)$$

and the I and S coefficients are preprogrammed for normalizing the concentration of the hemoglobin adduct to the total amount of hemoglobin in the sample; and d) means for dividing the normalized hemoglobin adduct concentration by the total hemoglobin concentration to obtain the corrected concentration of the hemoglobin adduct.

17. The device of claim 16 wherein the $2^{nd}$ order polynomial equation is used.

18. The device of claim 16 which also contains means for contacting the hemoglobin in the blood sample with a surfactant.

19. The device of claim 18 wherein the surfactant is a non-ionic, cationic or anionic detergent.

* * * * *